US012621617B2

(12) United States Patent
Popovac et al.

(10) Patent No.: US 12,621,617 B2
(45) Date of Patent: *May 5, 2026

(54) MUSICAL PERCEPTION OF A RECIPIENT OF AN AUDITORY DEVICE

(71) Applicant: Cochlear Limited, Macquarie University (AU)

(72) Inventors: Ivana Popovac, Dee Why (AU); Alexander von Brasch, Cremorne (AU); Justin James Gilmour, Camperdown (AU); Matthew Zygorodimos, Macquarie University (AU); Rishi Wadhwani, North Ryde (AU); James Davies, Macquarie University (AU)

(73) Assignee: Cochlear Limited, Macquarie University (AU)

( * ) Notice: Subject to any disclaimer, the term of this patent is extended or adjusted under 35 U.S.C. 154(b) by 281 days.

This patent is subject to a terminal disclaimer.

(21) Appl. No.: 18/497,138

(22) Filed: Oct. 30, 2023

(65) Prior Publication Data

US 2024/0089679 A1 Mar. 14, 2024

Related U.S. Application Data

(63) Continuation of application No. 17/294,529, filed as application No. PCT/IB2020/000481 on Jun. 15, 2020, now Pat. No. 11,843,919.

(Continued)

(51) Int. Cl.
| | |
|---|---|
| *H04R 25/00* | (2006.01) |
| *A61N 1/05* | (2006.01) |
| *A61N 1/36* | (2006.01) |

(52) U.S. Cl.
CPC ........... *H04R 25/70* (2013.01); *A61N 1/0541* (2013.01); *A61N 1/36031* (2017.08);
(Continued)

(58) Field of Classification Search
CPC .... H04R 25/70; H04R 25/507; H04R 25/606; H04R 2225/41; H04R 2225/67;
(Continued)

(56) References Cited

U.S. PATENT DOCUMENTS

| | | |
|---|---|---|
| 8,536,436 B2 | 9/2013 | Moreno |
| 9,338,567 B2 | 5/2016 | Mauger |

(Continued)

FOREIGN PATENT DOCUMENTS

| | | |
|---|---|---|
| KR | 1020000064472 A | 11/2000 |
| WO | 2010045358 A1 | 4/2010 |
| WO | 2012072141 A1 | 6/2012 |

OTHER PUBLICATIONS

International Search Report and Written Opinion in counterpart International Application No. PCT/IB2020/000481, mailed Oct. 27, 2020, 9 pages.

*Primary Examiner* — Tuan D Nguyen

(74) *Attorney, Agent, or Firm* — Edell, Shapiro & Finnan, LLC

(57) ABSTRACT

Treatment actions can be taken based on an analysis of the ability of a recipient of an auditory prosthesis to perceive musical activities. The occurrence of musical activities and the recipient's response thereto can be determined based on transducers. The recipient's musical perception can be determined by analyzing the signals from the transducers as stand-alone measures or by comparing the signals against known music. The treatment actions can relate to the treatment of a hearing-impairment of the recipient of the auditory prosthesis, such as by modifying the settings of the auditory (Continued)

prosthesis to affect the ongoing operation of the auditory prosthesis.

24 Claims, 8 Drawing Sheets

Related U.S. Application Data

(60)  Provisional application No. 62/862,181, filed on Jun. 17, 2019.

(52)  U.S. Cl.
CPC ..... *A61N 1/36038* (2017.08); *A61N 1/36139* (2013.01); *H04R 25/507* (2013.01); *H04R 25/606* (2013.01); *H04R 2225/41* (2013.01); *H04R 2225/67* (2013.01)

(58)  Field of Classification Search
CPC  H04R 25/603; A61N 1/0541; A61N 1/36031; A61N 1/36038; A61N 1/36139; A61N 1/36025; A61N 1/37252; A61F 11/045; A61B 5/293; A61B 5/374; A61M 21/00; A61M 2021/0027
See application file for complete search history.

(56)  References Cited

U.S. PATENT DOCUMENTS

| | | |
|---|---|---|
| 9,374,647 B2 | 6/2016 | Han et al. |
| 9,473,852 B2 | 10/2016 | Buyens |
| 9,826,318 B2 | 11/2017 | Pedersen et al. |
| 9,928,835 B1 | 3/2018 | Tang |
| 2014/0277276 A1 | 9/2014 | Saoji |
| 2015/0157860 A1 | 6/2015 | Bartel |
| 2017/0001008 A1 | 1/2017 | Hunt et al. |
| 2017/0359659 A1 | 12/2017 | Von Brasch et al. |
| 2018/0085581 A1 | 3/2018 | Fung et al. |
| 2018/0333577 A1 | 11/2018 | Nygard et al. |
| 2019/0090073 A1 | 3/2019 | Wendt et al. |

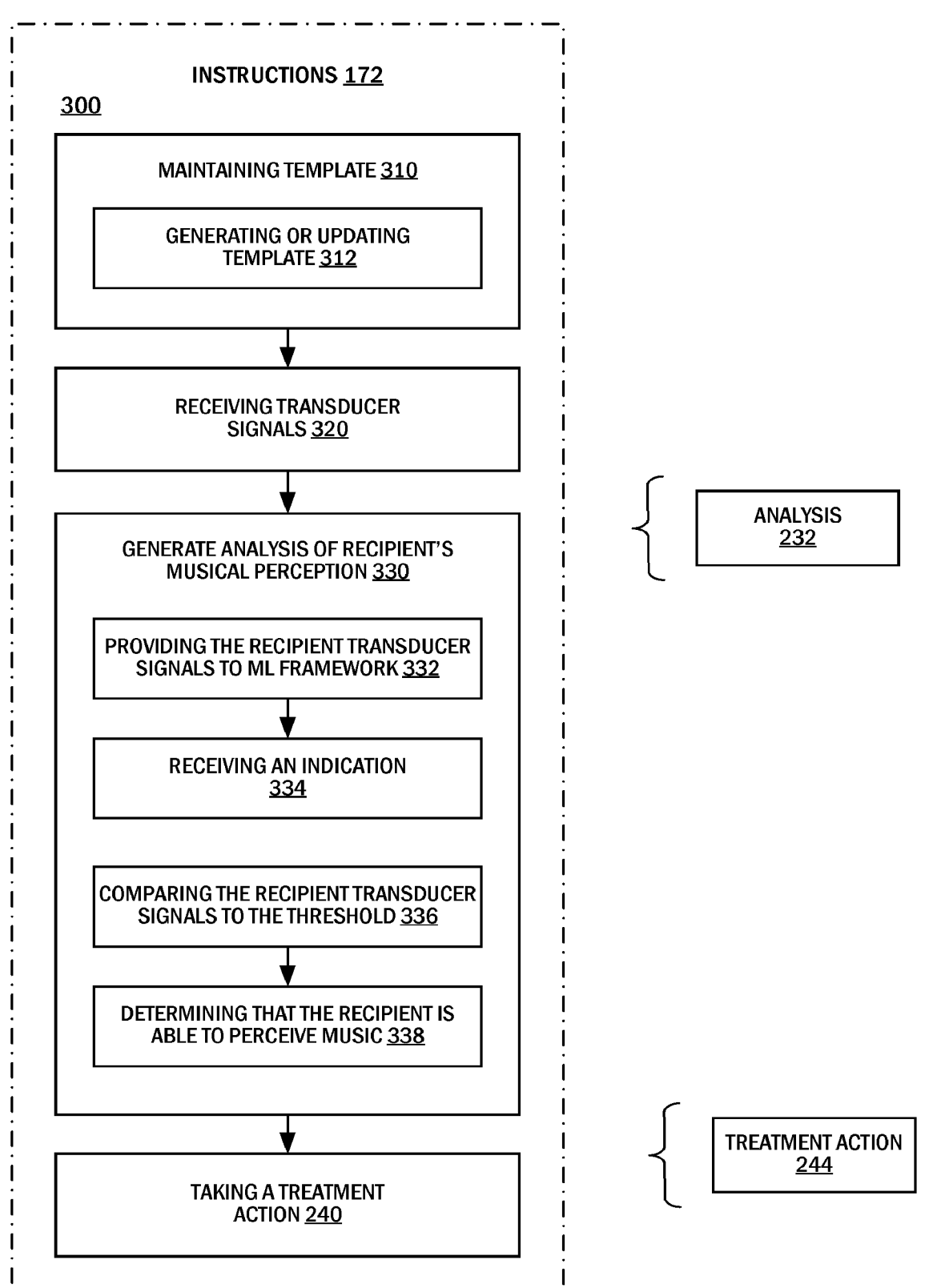

INSTRUCTIONS 172

300

MAINTAINING TEMPLATE 310

GENERATING OR UPDATING
TEMPLATE 312

RECEIVING TRANSDUCER
SIGNALS 320

GENERATE ANALYSIS OF RECIPIENT'S
MUSICAL PERCEPTION 330

PROVIDING THE RECIPIENT TRANSDUCER
SIGNALS TO ML FRAMEWORK 332

RECEIVING AN INDICATION
334

COMPARING THE RECIPIENT TRANSDUCER
SIGNALS TO THE THRESHOLD 336

DETERMINING THAT THE RECIPIENT IS
ABLE TO PERCEIVE MUSIC 338

TAKING A TREATMENT
ACTION 240

ANALYSIS
232

TREATMENT ACTION
244

FIG. 3

MUSICAL PERCEPTION OF A RECIPIENT OF AN AUDITORY DEVICE

This is a continuation of U.S. patent application Ser. No. 17/294,529, filed May 17, 2021, which is a National Stage Entry of PCT International Patent Application No. PCT/IB2020/000481, filed Jun. 15, 2020, which claims the benefit of priority to U.S. Provisional Patent Application No. 62/862,181, filed Jun. 17, 2019, the entire disclosure of which is incorporated by reference in its entirety.

BACKGROUND

Medical devices having one or more implantable components, generally referred to herein as implantable medical devices, have provided a wide range of therapeutic benefits to recipients over recent decades. In particular, partially or fully-implantable medical devices such as hearing prostheses (e.g., bone conduction devices, mechanical stimulators, cochlear implants, etc.), implantable pacemakers, defibrillators, functional electrical stimulation devices, and other implantable medical devices, have been successful in performing lifesaving and/or lifestyle enhancement functions and/or recipient monitoring for a number of years.

The types of implantable medical devices and the ranges of functions performed thereby have increased over the years. For example, many implantable medical devices now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, the implantable medical device.

SUMMARY

In an example, there is a computer-implemented process comprising: determining an occurrence of a musical activity proximate a recipient of an auditory prosthesis using first transducer signals from one or more first transducers; determining an indication of the recipient's ability to perceive the musical activity using second transducer signals from one or more second transducers; generating an analysis of the recipient's musical perception using the indication; and taking a treatment action relating to the recipient based on the analysis.

In another example, there is a process comprising: maintaining, at a server, a template defining an association between transducer signals and musical perception; receiving, at the server, recipient transducer signals associated with a recipient of an auditory prosthesis; using the template and the recipient transducer signals to generate an analysis of the recipient's musical perception; and taking a treatment action relating to the auditory prosthesis based on the analysis.

In another example, a computer-implemented process comprising: collecting transducer signals from one or more transducers associated with a recipient of an auditory prosthesis; generating indications of the recipient's musical perception using the transducer signals; generating an analysis of the recipient's musical perception using the indications; and taking a treatment action relating to the recipient using the analysis.

In another example, there is a system comprising: a server comprising: a processing unit a memory a template stored in the memory that defines an association between transducer signals and musical perception; instructions stored in the memory that, when executed by the processing unit cause the processer to: receive, from an auditory prosthesis application, recipient transducer signals associated with a recipient of an auditory prosthesis; generate an analysis of the recipient's musical perception using the template and the recipient transducer signals; and take a treatment action relating to the auditory prosthesis based on the analysis.

BRIEF DESCRIPTION OF THE DRAWINGS

The same number represents the same element or same type of element in all drawings.

FIG. 3 illustrates a second example process for taking a treatment action with respect to the musical perception of a recipient of an auditory prosthesis.

DETAILED DESCRIPTION

Figure 1:
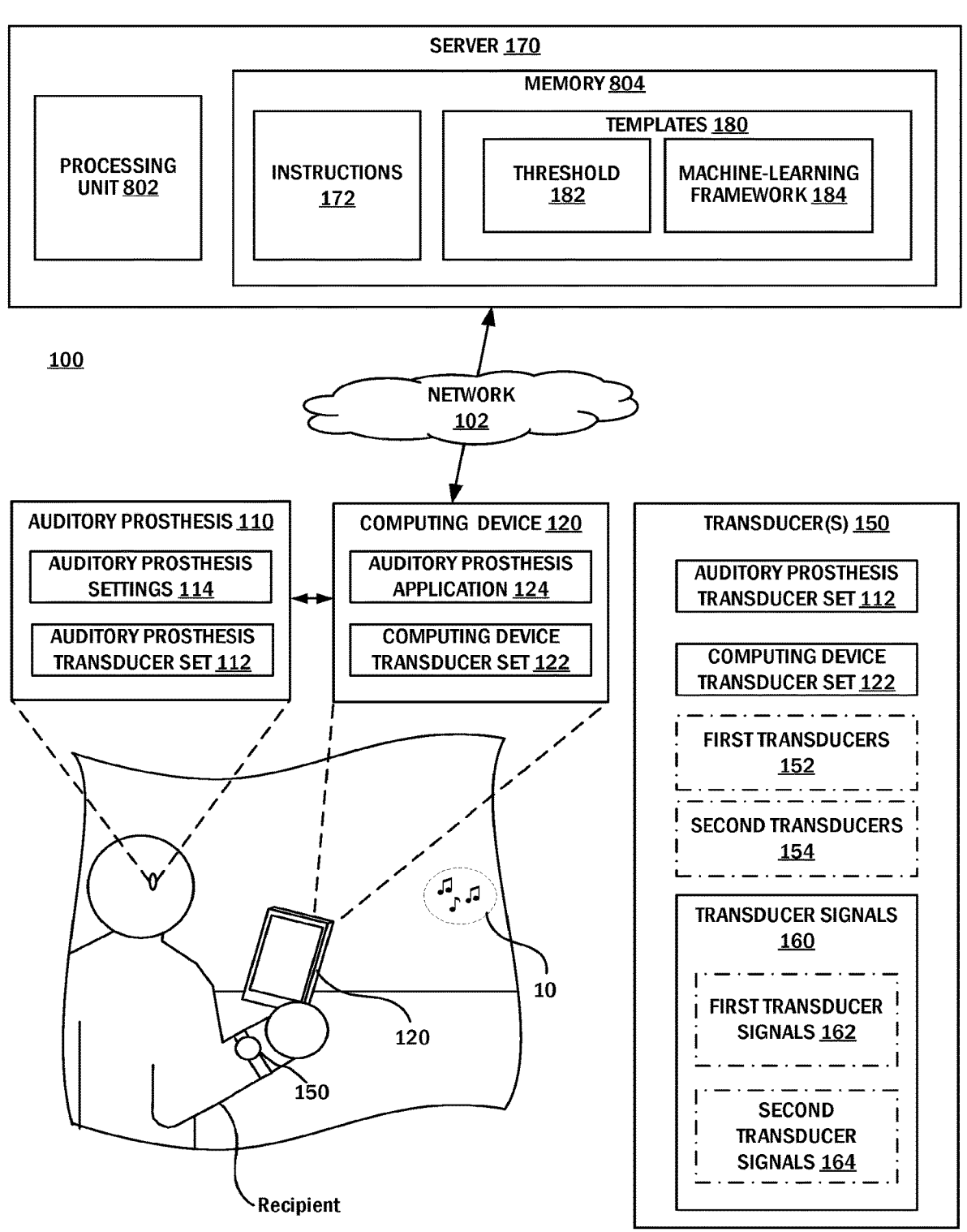
FIG. 1 illustrates an example system that includes an auditory prosthesis of a recipient and a computing device connected to a server over a network.

Hearing loss can affect a person's ability to perceive and appreciate music in addition to the ability to understand speech. Musical perception can encompass not only whether the recipient enjoys music but also whether the recipient is able to recognize music as distinct from noise or other kinds of sounds. Auditory prostheses can be used to treat hearing loss by causing hearing percepts in a recipient of the auditory prosthesis. But the hearing percepts caused by the auditory prosthesis do not always appropriately mimic natural hearing percepts. As a result, the recipient may be unable to perceive hearing percepts caused by musical input as actually being musical (e.g., the recipient may perceive musical input as mere noise). While the recipient can learn to understand music and thereby improve his or her musical perception, doing so can be difficult without assistance. Likewise, while the auditory prosthesis can be programmed to improve musical reproduction, doing so can be difficult and detrimental to the ability of the auditory prosthesis to reproduce human speech.

Often a trained professional (e.g. an audiologist) programs the auditory prosthesis during an initial fitting session. But, typically, the focus of the programming is the ability of the auditory prosthesis to reproduce human speech in a manner understandable by the recipient of the auditory prosthesis. If musical enjoyment is considered at all during the programming, the auditory prosthesis is typically programmed based on a psychophysical metric (e.g., spectral discrimination) or a subjective measure related to music determined during the fitting session. Once an acceptable level is reached, the process ends. After programming, the recipient may be instructed to perform rehabilitation activities (e.g. listening to music daily) or to monitor performance of the auditory prosthesis (e.g., by performing an assessment against a functional listening index). However, these techniques typically do not sufficiently address the recipient's ability to perceive music and the ability of an auditory prosthesis to satisfactorily reproduce music.

As a result, many individuals having hearing impairments are unable to enjoy music, even when assisted by an auditory prosthesis. For these individuals, the inability to enjoy music adversely affects their overall quality of life. Further, the perceived lack of benefit can even induce a nocebo effect, resulting in diminished outcomes across all performance metrics, not only musical metrics. The ability of the auditory prosthesis to reproduce music can contribute to the ability of the individual to enjoy music.

Examples disclosed herein are relevant to improving the musical perception of a recipient of an auditory prosthesis. Such improvements can be achieved through treatment actions taken based on an analysis of the recipient's ability to perceive musical activities as determined based on signals from transducers. The treatment actions can relate to the treatment of a hearing-impairment of the recipient of the auditory prosthesis.

In an example implementation, signals from transducers in the vicinity of the recipient are collected during everyday use of the auditory prosthesis by the recipient. The transducer signals can be used to determine whether and how the recipient is responding to musical activities. The transducers can include sensors of the auditory prosthesis itself, as well as transducers or sensors of personal devices associated with the recipient, such as a wearable device (e.g., smart watch or heartrate monitor) or mobile phone. For instance, an implanted microphone (e.g., of the auditory prosthesis) of the recipient can produce signals relating to blood flow (e.g., when the implanted microphone is placed near an artery) or respiratory activity (e.g., when the implanted microphone is placed near the noise/throat/chest). Increases in respiration and blood flow can correlate to a recipient's response to music. Likewise, implanted electrodes (e.g., of the auditory prosthesis) or external electrodes (e.g., headband-worn electrodes) can detect brainstem, midbrain, or cortical activation (e.g., if the electrodes are proximate the head or cochlea) indicative of a response to music. Next, the signals are processed to compute indications of the recipient's ability to perceive music. For instance, the transducer signals can be used to determine an indication by determining that the recipient is responding to music activity.

These indications are aggregated and logic is applied to compute an analysis (e.g., including performance metrics) related to the recipient's musical perception. The analysis can then be used as a trigger to perform one or more treatment actions relevant to helping the recipient to enjoy music. The transducer-based approach described above and herein advantageously allows for improvements to the recipient's ability to perceive music (e.g., via the treatment actions) in a manner that does not require a trained clinician, that can be performed in the individual's real world sound environment, and can be implemented in a recipient-friendly manner (e.g., in contrast to a clinical sound booth test). Further, in many cases, the approach can be implemented in a way that is transparent to the recipient. Disclosed systems and processes can automatically and independently determine that the recipient is in an environment where music should be perceived, analyze the recipient's music perception, and use the analysis to treat the recipient (e.g., the analysis can be used to automatically computing a functional listening index, to implement a rehabilitation program, or to modify settings of the auditory prosthesis). The recipient and his or her clinician may simply consume the data generated by the process, such as via periodic reports of progress provided based on the analysis. Further, the transducer-based approach can provide recipients with a tool to gauge engagement with music in an objective and quantifiable way. This can provide assurance that a new auditory prosthesis is working, and provide objective measures indicating that the recipient is improving.

Example System

FIG. 1 illustrates a system 100 with which one or more processes described herein can be implemented. As illustrated, the system 100 includes an auditory prosthesis 110 of a recipient and a computing device 120. The computing device 120 is connected to a server 170 over a network 102. In addition, one or more transducers 150 are located within the system 100. The figure shows the occurrence of a musical activity 10 proximate the recipient.

The musical activity 10 is the audible occurrence of music. The musical activity 10 can take any of a variety of forms, including pre-recorded music, live music, formal music (e.g., commercially-produced music), or informal music (e.g., a person singing or humming at a birthday party). The musical activity 10 can have various levels of prominence, such as in the background (e.g., music playing at restaurant) or in the foreground (e.g., at a concert). The musical activity 10 can include music being played via speakers or the playback of music via the auditory prosthesis 110 itself.

The network 102 is a computer network, such as the Internet, that facilitates the electronic communication of data among computing devices connected to the network 102.

Example System—Auditory Prosthesis

The auditory prosthesis 110 is an apparatus relating to the recipient's auditory system (e.g., an auditory device). In many examples, the auditory prosthesis 110 is a medical device configured to treat a hearing-impairment of the recipient. The auditory prosthesis 110 can take a variety of forms including a cochlear implant, an electroacoustic device, a percutaneous bone conduction device, a passive transcutaneous bone conduction device, an active transcutaneous bone conduction device, a middle ear device, a totally-implantable auditory device, a mostly-implantable auditory device, an auditory brainstem implant device, a tooth-anchored hearing device, other auditory prostheses, and combinations of the foregoing (e.g., binaural systems that include a prosthesis for a first ear of a recipient and a prosthesis of a same or different type for the second ear). Example implementations of the auditory prosthesis 110 are described in more detail in FIG. 5 (showing a cochlear implant), FIG. 6 (showing a percutaneous bone conduction device), and FIG. 7 (showing a transcutaneous bone conduction device). In the illustrated example, the auditory prosthesis 110 includes an auditory prosthesis transducer set 112 and operates according to auditory prosthesis settings 114. Technology disclosed herein can be used with auditory devices such as consumer auditory devices (e.g., a hearing aid or a personal sound amplification product)

The auditory prosthesis transducer set 112 can be a collection of one or more components of the auditory prosthesis 110 that generate transducer signals based on sensed occurrences, such as data regarding the environment around the auditory prosthesis 110, the auditory prosthesis 110 itself, or the recipient. In many examples, the auditory prosthesis transducer set 112 includes an external microphone. The auditory prosthesis transducer set 112 can include one or more other sensors, such as one or more implanted microphones, accelerometers, gyroscopic sensors, location sensors, telecoils, cameras, pupilometers, biosensors (e.g., heart rate or blood pressure sensors), and light sensors, among others. The auditory prosthesis transducer set 112 can include components disposed within a housing of the auditory prosthesis 110 as well as devices electrically coupled to the auditory prosthesis 110 (e.g., via wired or wireless connections).

In examples, the auditory prosthesis transducer set 112 includes a remote device connected to the auditory prosthesis 110 via an FM (Frequency Modulation) connection, such as a remote microphone (e.g., a COCHLEAR TRUE WIRELESS MINI MICROPHONE2+), a television audio streaming device, or a phone clip device, among other devices having FM transmission capabilities. The auditory prosthesis transducer set 112 can further include sensors that obtain data regarding usage of the auditory prosthesis 110, such as software sensors operating on the auditory prosthesis 110 that track data such as: when the auditory prosthesis 110 is worn by the recipient, when the auditory prosthesis 110 (e.g., an external portion thereof) is removed from the recipient, when one or more of the auditory prosthesis settings 114 are modified, a current scene mode in which the auditory prosthesis 110 is operating (e.g., as determined by a scene classifier), and how long the auditory prosthesis 110 is operated using particular settings of the auditory prosthesis settings 114, among other data.

In examples, the auditory prosthesis transducer set 112 can further include a scene classifier. A scene classifier is software that obtains data regarding the environment around the auditory prosthesis (e.g., from one or more other sensors of the auditory prosthesis transducer set 112) and determines a classification of the environment. Possible classifications can include, for example, speech, noise, and music, among other classifications. The auditory prosthesis 110 can then use the classification to automatically alter the auditory prosthesis settings 114 to suit the environment 101. For example, when the scene classifier determines that the environment around the prosthesis is windy, a wind-noise scene can be selected to automatically modify the auditory prosthesis settings 114 to ameliorate wind noise. In another example, the scene classifier can determine that music is occurring nearby and automatically modify the auditory prosthesis settings 114 to improve musical reproduction. An example scene classifier is described in US 2017/0359659, filed Jun. 9, 2016, and entitled "Advanced Scene Classification for Prosthesis", which is incorporated by reference herein in its entirety for any and all purposes.

The auditory prosthesis settings 114 are one or more parameters having values that affect how the auditory prosthesis 110 operates. For example, the auditory prosthesis 110 receives sound input from the environment (e.g., using a microphone of the auditory prosthesis 110), converts the sound input into a stimulation signal, and uses the stimulation signal to produce stimulation (e.g., vibratory or electrical) to cause a hearing percept in the recipient. The auditory prosthesis settings 114 are typically stored in memory on the auditory prosthesis 110.

The auditory prosthesis settings 114 can include a map having minimum and maximum stimulation levels for frequency bands of stimulation channels. The map is then used by the auditory prosthesis 110 to control an amount of stimulation to be provided. For instance, where the auditory prosthesis 110 is a cochlear implant, the map affects which electrodes of the cochlear implant to stimulate and in what amount based on a received sound input. In some examples, the auditory prosthesis settings 114 include two or more predefined groupings of settings selectable by the recipient. One of the two or more predefined groupings of settings may be a default setting.

The auditory prosthesis settings 114 can also include sound processing settings that modify sound input before the sound input is converted into a stimulation signal. Such settings can include, for example, particular audio equalizer settings can boost or cut the intensity of sound at various frequencies. In examples, the auditory prosthesis settings 114 can include a minimum threshold for which received sound input causes stimulation, a maximum threshold for preventing stimulation above a level which would cause discomfort, gain parameters, loudness parameters, and compression parameters. The auditory prosthesis settings 114 can include settings that affect a dynamic range of stimulation produced by the auditory prosthesis 110. As described above, many of the auditory prosthesis settings 114 affect the physical operation of the auditory prosthesis 110, such as how the auditory prosthesis 110 provides stimulation to the recipient in response to sound input received from the environment 101. Examples of settings, settings modification, and pre-processing are described in U.S. Pat. Nos. 9,473,852 and 9,338,567, which are both incorporated herein by reference for any and all purposes.

Example System—Computing Device

The computing device 120 is a computing device associated with the recipient of the auditory prosthesis 110. In many examples, the computing device 120 is a cell phone, tablet, smart watch, or heart rate monitor, but can take other forms. Although described primarily in the context of the recipient, the computing device 120 can be a computing device owned or primarily used by a parent or caregiver for the recipient. The computing device 120 can be in communication with the server 170, such as via the auditory prosthesis application 124 communicating over the network 102. In the illustrated example, the computing device 120 includes a computing device transducer set 122 and an auditory prosthesis application 124.

The computing device transducer set 122 is group of one or more components of the computing device 120 that obtains data. The computing device transducer set 122 can include one or more sensors, such as microphones, accelerometers, gyroscopic sensors, location sensors, biosensors (e.g., heart rate or blood pressure sensors), and light sensors, among others. The computing device transducer set 122 can include components disposed within a housing of the computing device 120 as well as devices electrically coupled to the computing device 120 (e.g., via wired or wireless connections). In some examples, the computing device transducer set 122 includes software sensors, such as software that obtains data from one or more data streams (e.g., audio streamed from the computing device 120 to the auditory prosthesis 110). The computing device transducer set 122 can further include sensors that obtain data regarding how the computing device 120 itself is being used.

In examples, the computing device 120 includes an auditory prosthesis application 124 that operates on the computing device 120 and cooperates with the auditory prosthesis 110. The auditory prosthesis application 124 is a computer program stored as computer-executable instructions in memory of the computing device 120 that, when executed, performs one or more tasks relating to the auditory prosthesis 110. For instance, the auditory prosthesis application 124 can control the auditory prosthesis 110 (e.g., by modifying the auditory prosthesis settings automatically or based on input received at the computing device 120 from the recipient), monitor usage of the auditory prosthesis 110, and obtain data from the auditory prosthesis 110. The computing device 120 can connect to the auditory prosthesis 110 using, for example, a wireless radiofrequency communication protocol (e.g., BLUETOOTH). The auditory prosthesis application 124 can transmit or receive data from the auditory prosthesis 110 over such a connection. The auditory prosthesis application 124 can be used to stream audio to the auditory prosthesis 110, such as from a microphone of the computing device transducer set 122 or an application running on the computing device 120 (e.g., a video or audio application). In other examples, another application running on the computing device 120 can stream audio to the auditory prosthesis 110. In examples, the auditory prosthesis application 124 functions as part of the computing device transducer set 122 by obtaining data regarding the auditory prosthesis 110.

Example System—Transducers

A transducer 150 of the transducers 150 is a component that produces transducer signals 160 responsive to a detected condition. In an example, the transducers 150 can include one or more of the following kinds of transducers: one or more movement sensors configured to provide movement sensor signals, one or more implanted microphones configured to provide body noise signals, one or more otoacoustic emission sensors configured to provide otoacoustic emission signals, one or more implanted electrodes configured to provide implanted electrode sensor signals, one or more external electrodes (e.g., headband-worn electrodes or adhered electrodes) configured to provide external electrode sensor signals, one or more EEG (electroencephalography) sensors configured to provide EEG signals, one or more program sensors configured to provide signals relating to the operation of a program, and one or more external microphones configured to provide one or more external microphone signals. The movement sensors can be any of a variety of different kinds of movement sensors. For example, the movement sensors can include accelerometers or gyroscopes, such as accelerometers or gyroscopes of the auditory prosthesis 110 or the computing device 120. The transducers 150 can be located in any of a variety of locations in the system 100. For example, as illustrated, the transducers 150 include the auditory prosthesis transducer set 112 and the computing device transducer set 122. The transducers 150 can be located elsewhere, such as in a wearable transducer (e.g., as may be found in a smart watch) worn by the recipient.

As illustrated, the transducers 150 can include two or more sub-groups of transducers 150, such as first transducers 152 and second transducers 154. The groups can indicate any physical or logical division of the transducers 150. In an example, the first transducers 152 are transducers 150 configured produce first transducer signals 162 indicative of whether a musical activity 10 is occurring in the proximity of the recipient. In an example, the second transducers 154 are transducers 150 configured to produce second transducer signals 164 indicative of the recipient's musical perception. In examples, there can be overlaps between the groups (e.g., a same transducer can be in multiple sub-groups of transducers). In other examples, the groups do not overlap.

A transducer signal 160 of the transducer signals 160 is data produced by a transducer 150. A transducer signal 160 can take any of a variety of different forms depending on the configuration of the transducer 150 that produced the transducer signal 160. Further, the form and character of the transducer signals 160 can change as the transducer signals 160 are used and moved throughout the system 100. For example, a transducer signal 160 can begin as a real-time analog signal that is converted into a real-time digital signal within a transducer 150, which is then transmitted in real-time packets of data to the auditory prosthesis application 124 for batch sending (e.g., non-real-time) to the server 170. Additionally, the transducer signals 160 can be processed as the transducer signals 160 are used and moved throughout the system 100. For instance, the transducer signals 160 can be converted into a standardized format and have relevant metadata attached (e.g., timestamps, transducer identifiers, etc.).

Example System—Server

The server 170 is a server computing device remote from the auditory prosthesis 110, and the computing device 120. The server 170 is communicatively coupled to the computing device 120 via the network 102. In many examples, the server 170 is indirectly communicatively coupled to the auditory prosthesis 110 through the computing device 120 (e.g., via the auditory prosthesis application 124). In some examples, the server 170 is directly communicatively coupled to the auditory prosthesis 110. In certain implementations, the auditory prosthesis 110 and the computing device 120 can be considered client devices of the server 170. In some examples, the functionality provided by the server 170 or the components thereof (e.g., the instructions 172 and the templates 180) can be provided by or located on a device local to the recipient (e.g., the computing device 120 or the auditory prosthesis 110). The auditory prosthesis application 124 can be a client application configured to interact with the server 170. The server 170 includes a processing unit 802 and a memory 804, which are described in more detail in FIG. 8. The server 170 further includes instructions 172 and one or more templates 180 stored in the memory 804.

Figure 2:
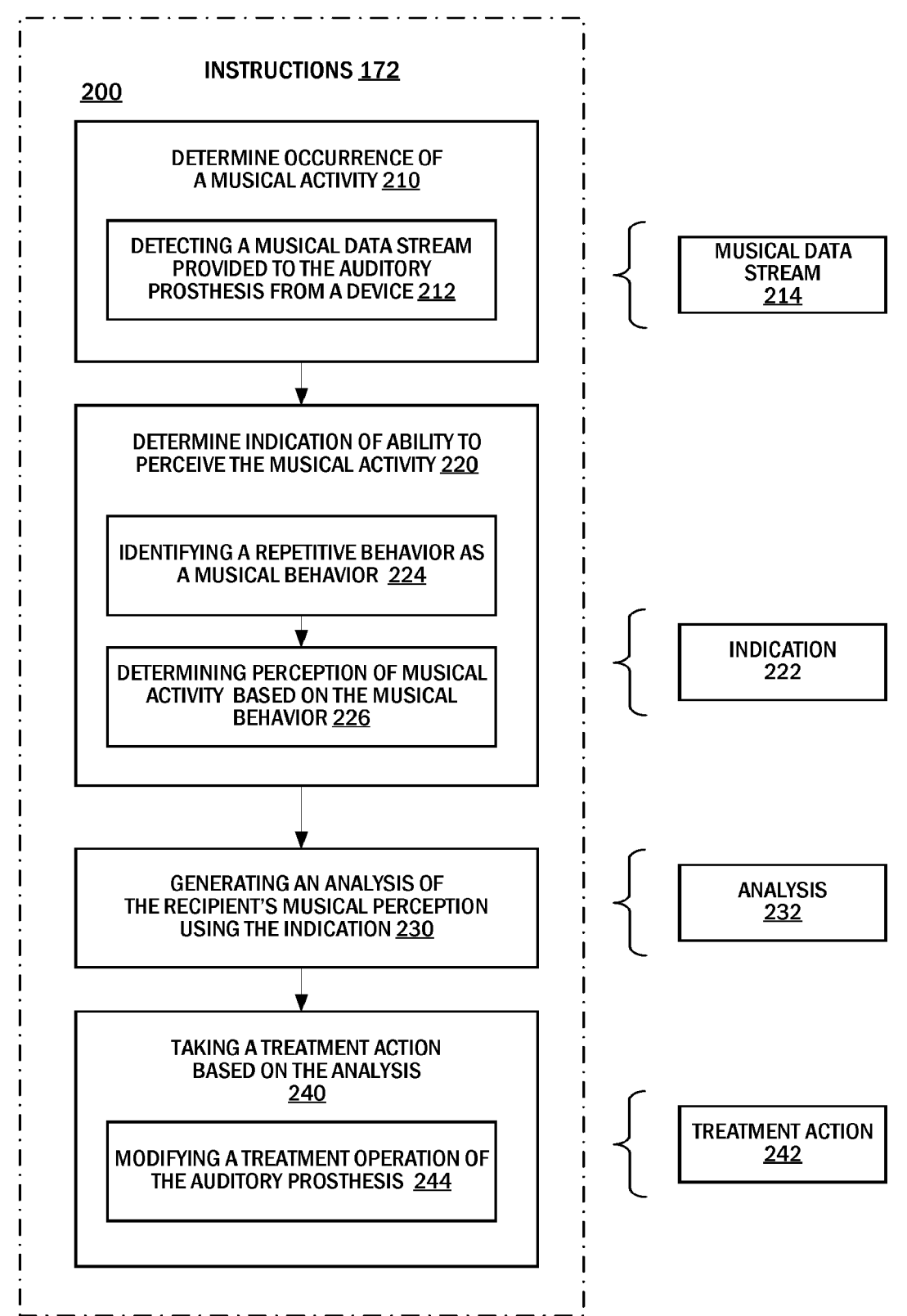
FIG. 2 illustrates a first example process for taking a treatment action with respect to the musical perception of a recipient of an auditory prosthesis.
Figure 4:
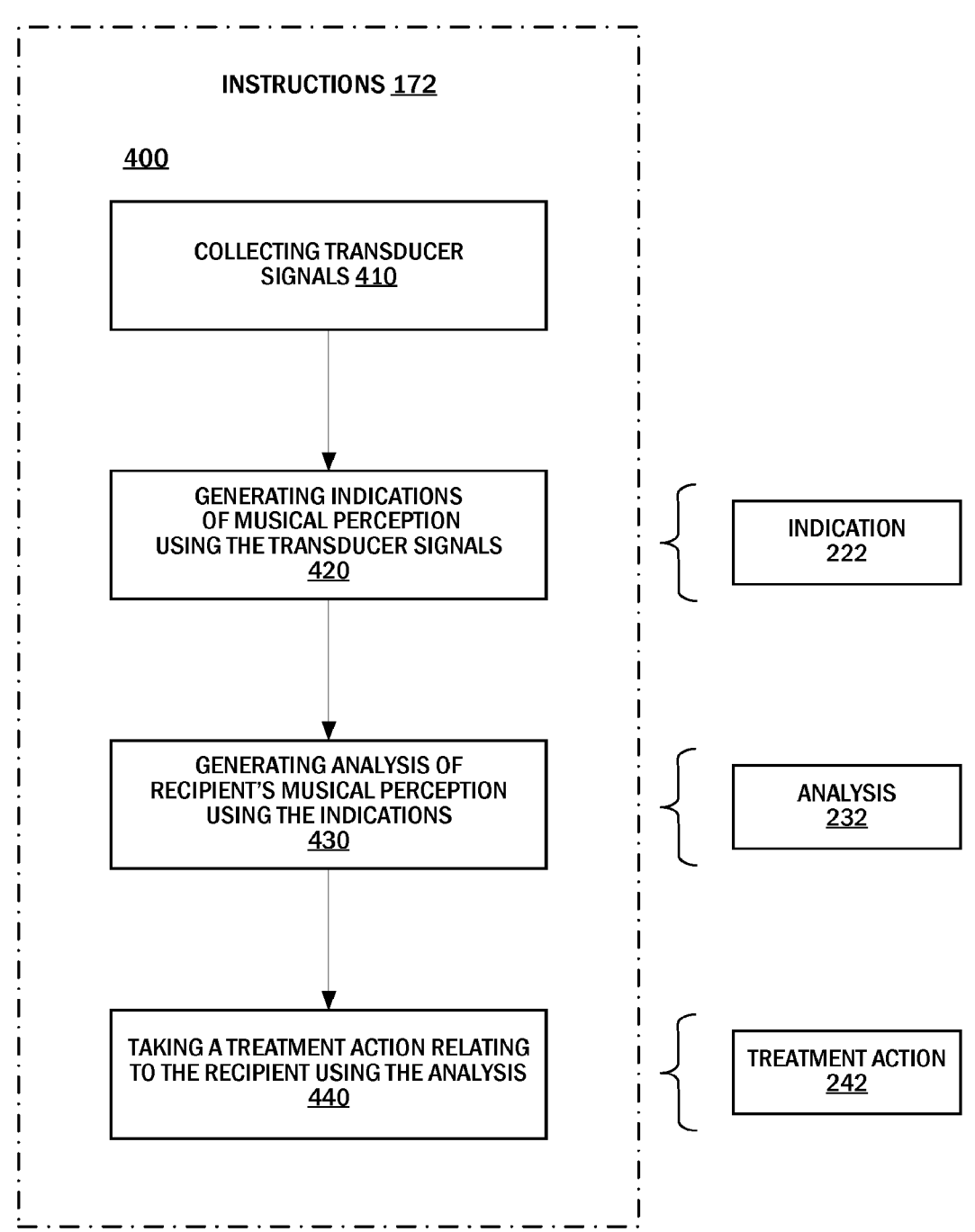
FIG. 4 illustrates a third example process for taking a treatment action with respect to the musical perception of a recipient of an auditory prosthesis.

The instructions 172 are processor-executable program instructions that, when executed by the processing unit 802 cause the processing unit 802 to perform actions or operations, such as the described in the processes of FIGS. 2-4.

A template 180 of the one or more templates 180 can be, for example, a reference, comparator, or translator with or against which obtained data (e.g., the signals or the indications) can be processed. For instance, the templates 180 can include data structures defining values of transducer signals that are or are not indications of whether the recipient is or is not responding to music. The templates 180 can include templates 180 that are personalized or non-personalized with respect to particular recipients. For example, during fitting of the auditory prosthesis 110, the recipient can be exposed to music and the objective reaction of the recipient (e.g., as measured via the transducers 150) is measured and stored as a personalized template 180 for the recipient against which future transducer signals 160 can be compared. In another example, objective reactions to music by multiple people (e.g., a statistically significant sample size of people) are measured and stored as a template against which specific individuals can be compared. Further, the one or more templates 180 can be created or curated by one or more clinicians. The templates 180 can take a variety of different forms, including one or more thresholds 182 and one or more machine-learning frameworks 184.

In some examples, the one or more templates 180 include one or more thresholds 182 against which the transducer signals 160 or indications can be compared. The thresholds 182 can describe, for example, a range or particular value that the transducer signals 160 can be compared against for use in processes described herein. For instance, the threshold 182 can define a tempo range in which a repetitive behavior is considered to be indicative of a musical activity (e.g., tempo in the range of 0.4 Hz-4 Hz can be indicative of dancing, clapping, or otherwise moving with perceived music).

In examples, the template 180 includes a trained machine-learning framework 184 configured to receive transducer signals 160 as input and provide an output based thereon (e.g., an indication of an ability to perceive music). In examples, the trained machine-learning framework 184 includes a neural network.

A machine-learning framework 184 is software and associated data that implements machine-learning capabilities. In many examples, the machine-learning framework 184 includes two primary components: a machine-learning model and an interface. The machine-learning model is a structured representation of the learning, such as how learning is achieved and what has been learned. For example, where the machine-learning model includes a neural network, the machine-learning model can define the representation of the neural network (e.g., the nodes of the neural network, the connections between the nodes, the associated weighs, and other data), such as via one or more matrices or other data structures. In another example, where the machine-learning model includes a decision tree, the machine-learning model can define the decision tree (e.g., the nodes of the decision tree and the connections therebetween). The machine-learning model can include multiple different types of machine-learning techniques. For example, the machine-learning model can define multiple different neural networks, decision trees, and other machine-learning techniques and their connections therebetween. For instance, output of a first neural network can flow to the input of a second neural network with the output therefrom flowing into a decision tree to produce a final output. The interface defines a software interface used in conjunction with the model. For example, the interface can define functions and processes for providing input to, receiving output from, training, and maintaining the machine-learning model. One or more aspects of the machine-learning framework 184 may be implemented with machine-learning toolkits, such as: TENSORFLOW by GOOGLE INC. of Mountain View, California; OPENAI GYM by OPENAI of San Francisco, California; or MICROSOFT AZURE MACHINE LEARNING by MICROSOFT CORP. of Redmond, Washington.

The machine-learning framework 184 can be trained or otherwise configured to receive data (e.g., one or more transducer signals 160 from one or more of the transducers 150) as input and provide an output based thereon. For example, there can be a machine-learning framework trained and configured to receive accelerometer and gyroscope signals as input and provide an indication whether the signals are indicative of whether the recipient is able to perceive music (e.g., whether the recipient is responding to music).

Example Processes

FIGS. 2-4 illustrate example processes for taking a treatment action with respect to the musical perception of a recipient of an auditory prosthesis 110. The processes can be performed using a system, such as the one described in FIG. 1. One or more aspects of the processes (e.g., one or more of the operations thereof) can be implemented as one or more instructions stored as part of the instructions 172.

Example Processes—First Example Process

FIG. 2 illustrates a first example process 200 for taking a treatment action with respect to the musical perception of a recipient of an auditory prosthesis 110. As illustrated, the process 200 begins with operation 210.

Operation 210 includes determining an occurrence of a musical activity 10. In an example, the operation 210 includes determining the occurrence of the musical activity 10 proximate the recipient of the auditory prosthesis 110 using first transducer signals 262 from one or more first transducers 152. The occurrence of the musical activity 10 proximate the recipient can be determined in any of a variety of ways. In an example, the occurrence of the musical activity 10 can be determined responsive to the auditory prosthesis 110 operating in a music-specific sound processing mode based on a determination by a scene classifier of the auditory prosthesis 110. In an example, the occurrence of the musical activity can be determined responsive to receiving input from the recipient (e.g., at the computing device 120) indicating that a musical activity 10 is occurring.

As another example, operation 210 can include determining the occurrence of a musical activity 10 proximate the recipient based on location data. The location data can be useful in determining whether the recipient is in a location where a musical activity 10 is likely to take place (e.g., a concert venue or a restaurant that may have background music). In an example, location data can include satellite-based location data (e.g., GPS-based location data) generated by the computing device 120. In another example, the location data is based on nearby wireless broadcasts, such as WI-FI SSIDs (Service Set Identifiers). Such wireless broadcasts can be useful for determining a current location as well as a current location type. For instance, while the auditory prosthesis 110 is operating in a music venue, the computing device 120 may detect a WI-FI SSID called "Music Venue Wi-Fi", which can be used as an indication that a musical activity 10 is occurring.

In an example, the transducer signals 160 can be used to determine the occurrence of the musical activity 10. For instance, an external microphone (e.g., of the auditory prosthesis transducer set 112) can produce an audio transducer signal indicative of the sonic environment proximate the recipient. The audio transducer signal can be analyzed (e.g., at the auditory prosthesis 110, the computing device 120, the server 170, or combinations thereof). In an example, the audio transducer signal can be analyzed to determine whether the qualities of the audio transducer signal indicate the occurrence of the musical activity 10. For example, the frequencies, amplitude modulation, and spectral spread of the audio transducer signal can be analyzed (e.g., using templates 180) to determine whether a threshold of likelihood is satisfied that indicates the occurrence of a musical activity. In another example, the audio transducer signal can be analyzed to determine not only whether a musical activity 10 is occurring but also a kind of musical activity 10 and identification of metadata regarding the musical activity 10. The kind and metadata can be determined by, for example, performing audio fingerprinting on the audio transducer signal to identify the specific music content being played and then obtaining metadata based on the identifier. Performing audio fingerprinting can include transmitting a portion of the audio transducer signal as input to an audio fingerprinting service (e.g., as may be provided by GRACENOTE, SHAZAM, or SOUNDHOUND) and receiving an identification of the musical activity 10 (if available) and metadata relating the audio transducer signal as output therefrom.

In examples, the templates 180 include one or more templates relating to the determining of the occurrence of a musical activity 10. For example, there may be one or more thresholds 182 relating to spectral characteristics or tempo that, when satisfied, indicate that a musical activity 10 occurred. In another example, the templates include one or more machine-learning frameworks 184 trained to receive transducer signals 160 as input and, as output, provide a prediction regarding whether or not a musical activity 10 occurred.

The occurrence of the musical activity 10 can be based on a data stream such as is described in operation 212.

Operation 212 includes detecting 212 a musical data stream 214 provided to the auditory prosthesis 110 from a computing device 120. The musical data stream 214 is a stream of musical data from a source (e.g., the computing device 120) to the auditory prosthesis 110 to cause a hearing percept in the recipient. The musical data stream 214 can take a variety of forms and can be provided to the auditory prosthesis 110 in any of a variety of manners. In an example, the musical data stream 214 can be a data stream over a radiofrequency connection (e.g., via BLUETOOTH or WI-FI) between the computing device 120 (e.g., a smartphone) and the auditory prosthesis 110. The musical data stream 214 can be detected in any of a variety of manners. In an example, the auditory prosthesis 110 detects the musical data stream 214 and provides a transducer signal 160 indicated that the auditory prosthesis is receiving the musical data stream 214. In an example, the computing device 120 detects that the computing device 120 is providing the musical data stream 214 and provides a transducer signal 160 indicating that it is providing the musical data stream 214 to the auditory prosthesis 110. In an example, the auditory prosthesis application 124 provides the musical data stream and detects the musical data stream 214. The transducer signal 160 regarding the musical data stream can further include metadata regarding the musical data stream 214, such as the name of the song, artist, album, or genre of the musical activity 10 provided by the musical data stream 214. Responsive to detecting 212 the musical data stream 214 being provided to the auditory prosthesis, it is determined that musical activity 10 occurred. Following operation 210, the flow of the process 200 can move to operation 220.

Operation 220 includes determining an indication 222 of the recipient's ability to perceive the musical activity 10. In an example, operation 220 is performed responsive to determining the occurrence of the musical activity 10 in operation 210. By performing the operation 220 responsive to detecting the musical activity 10, computing resources (e.g., network bandwidth, processing cycles, and battery life) can be conserved by avoiding using resources to determine a recipient's ability to perceive music when no music is present. In other examples, it can nonetheless be beneficial for operation 220 to be performed whether or not the musical activity 10 is detected. For example, performing operation 220 absent a detected musical activity 10 can be performed to obtain negative data against which future data can be compared. In other words, it can be beneficial for the system 100 to obtain data regarding how the recipient behaves when a musical activity 10 is not occurring to better determine whether how the recipient behaves when a musical activity 10 is occurring.

The indications 222 can be determined based on whether (and, in some implementations, to what extent) the recipient is able to perceive the musical activity 10. In an example, the indication 222 of the recipient's ability to perceive music is data relevant to and suggestive of whether the recipient is able to perceive music. The suggestiveness can be relative to a threshold 182 (e.g., the data more likely than not indicates that the recipient is able to or is not able to perceive the musical activity 10). The determination of an indication 222 can take a variety of forms. In an example, the indication 222 can include simply a binary indication of whether the recipient perceived a musical activity 10. In a further example, the indication 222 can include a relative degree to which the recipient is able to perceive music. In still further examples, the indication 222 can include metadata regarding the indication 222 and the musical activity 10. In some implementations, there can be a single indication 222 determined for each musical activity 10. In other implementations, there can be multiple indications 222 per musical activity 10. For instance, the indication 222 can include or be based on an aggregation of transducer signals 160 from multiple transducers 150, or there can be an indication 222 for each set of transducer signals 160 received relating to the musical activity 10 (e.g., for a single musical activity 10, there can an indication 222 based on microphone data that the recipient is not perceiving the musical activity 10 and there can be an indication 222 based on movement data that the recipient is perceiving the musical activity 10). The determining of the indication 222 can include using transducer signals 160 from the transducers 150, such as the second transducer signals 164 from one or more second transducers 154. Transducer signals 160 contemporaneous with the musical activity 10 can be analyzed to determine whether there is an indication 222 that the recipient perceived the musical activity 10.

As an example, the operation 220 can include determining an indication 222 based on a change in breathing rate or heart rate, which can relate to a rate of activity, such as a vigorousness of an individual's dancing, singing, or other engagement with music. This determination can be based on transducer signals 160 such as sounds relating to respiratory activity and blood flow obtained from transducers 150 such as implantable microphones.

As another example, the operation 220 can include determining an indication 222 based on neural activation. Neural activation can be indicative of emotional or high-level engagement with or perception of music. The determination can be based on transducer signals 160 such as electrode or EEG signals processed to compute power in particular spectral bands (e.g., cortical frequency bands, such as alpha, beta, gamma, delta waves) from transducers 150 such as implantable electrodes or EEG sensors.

As another example, operation 220 can include determining an indication 222 based on certain kinds of speaking, singing, rapping, or humming, such as may be determined from the rate, volume, duration, fundamental frequency, pitch, and spectral properties of received microphone signals.

As another example, operation 220 can include determining an indication 222 based on user input received from the recipient. For example, operation 220 can include, responsive to determining the occurrence of the musical activity 10, sending a notification to the recipient asking the recipient one or more questions regarding the musical activity 10, such as whether the recipient can hear the musical activity 10 and how the recipient rates his or her experience of the musical activity 10. The response from the recipient can be used to determine the indication 222.

As another example, operation 220 can include determining an indication based on movement sensor signals. For example, based on transducer signals 160, an indication 222 can be determined that the recipient is moving his or her head or hands in time to music. This manner of determining is described in more detail in relation to operation 224.

The transducer signals 160 can be analyzed in a variety of ways to determine the indications 222. For example, the transducer signals 160 can be compared to a template 180. The template 180 can be predefined, can be learned based on prior recordings of the recipient's response, or can be learned based on prior records of other individuals' responses. In some examples, the template can define features of known music (e.g. tempo, melody). For example, the movement signals can be compared to features of a known or simultaneously detected musical signal such that it can be determined whether a motion of the recipient is a similar frequency to the tempo of music or whether the recipient is singing in a harmonious way with the melody of the music or is synchronous with vocals of the music. In this manner, the indication 222 can include not only whether the recipient perceives the musical activity 10 but also the extent to which the recipient is able to perceive the musical activity 10. For instance, the harmony between the recipient singing and the musical activity 10 itself can be compared. The music signal can be detected in any of a variety of ways, such as those described above in operation 210. In addition or instead, the recipient's activity can be compared with activity of other individuals that are known to be experiencing the same musical activity 10. For instance, it can be determined whether the recipient is moving in a similar way to a dance partner or another member of a flash mob. Such a determination can result in determining of the indication 222.

In some examples, operation 220 includes operation 224 and operation 226.

Operation 224 includes identifying a repetitive behavior having a frequency as being a musical behavior. For example, the repetitive behavior can be identified as being a musical behavior responsive to the frequency being within a typical musical tempo range (e.g., 0.4 Hz-4 Hz) because such behavior can be indicative of dancing, clapping, or otherwise moving with perceived music. Such behavior can be identified using signals from one or more movement transducers. In another example, the repetitive behavior can be identified as being a musical behavior responsive to the frequency matching (e.g., being within a threshold amount) a frequency of the musical activity 10 identified in operation 210. Following operation 224, the flow can move to operation 226.

Operation 226 includes determining whether the recipient is able to perceive the musical activity 10 based on the musical behavior. For example, responsive to the repetitive behavior being identified as a musical behavior, the indication 222 is determined to be that the recipient is able to perceive the musical activity 10. In some examples, responsive to the repetitive behavior being identified as a non-musical behavior, the indication 222 is determined to be that the recipient is unable to perceive the musical activity 10. In an example, an extent of the motion is used to determine an extent of engagement with the musical activity 10 (e.g. more motion implies more engagement with music activity).

In some examples, operation 226 includes determining whether the recipient is responding to an auditory cue or a cue provided by another sense. For example, in some instances, the repetitive behavior or another response from the recipient may be influenced by a non-auditory cue rather than from the recipient perceiving the musical activity 10 through the auditory prosthesis 110. For instance, the recipient may be responding to visual cues provided by movement of others around the recipient (e.g., the recipient is clapping in time to music based on seeing other clap rather than hearing the beats) or by a music visualizer or video played in conjunction with the audio (e.g., the recipient may respond to visual cues provided by watching a music video rather than listening to the music). As another example, the recipient may feel the music (e.g., by physically feeling the bass component of the music or by feeling the movement of a dance partner) and respond to the tactile feeling rather than the auditory component of the music. As such, the operation 226 can include determining whether and to what extent the recipient may be influenced by non-audio cues and using such a determination in the generation of the indication 222. For instance, operation 220 can determine that the recipient is responding to the musical activity 10 but that the response is due to non-audio cues. Responsive to such a determination, the indication 222 can be set to indicate that the recipient is unable to perceive the musical activity 10 or that the recipient is less able to perceive the musical activity 10 than would otherwise have been indicated. The determination of the non-audio cues can be made by measuring the non-audio cues using the transducers 150. For example, a camera can be used to measure whether and to what extent visual cues exist. In another example, transducers 150 can be used to determine whether the recipient is viewing a music video (e.g., which may provide visual cues) or is listening to music via headphones (e.g., which may indicate that the recipient is not feeling bass from speakers). Compensating for behavior caused by non-auditory cues can increase the accuracy by improving the quality of data used by the process 200.

Following operation 220, the flow of the process 200 can move to operation 230.

Operation 230 includes generating an analysis 232 of the recipient's musical perception using the one or more indications 222. The transducer signals 160, indications 222, and other associated data can be aggregated on the auditory prosthesis 110, the computing device 120 associated with the recipient (e.g., a mobile phone), or on the server 170 and used to form an analysis 232 of the recipient's musical perception. In examples, the analysis 232 is data that represents conclusions or inferences generated based on the transducer signals 160, indications 222, and other associated data regarding the recipient's musical perception. The analysis 232 can be generated based on one or more indications 222 relating to one or more musical activities 10. The analysis 232 can be generated based on a comparison of the indications over time, such as how the recipient's musical perception has changed. In an example, the recipient's musical perception is measured during a clinical visit (e.g., during an initial fitting of the auditory prosthesis 110 or during a check-up appointment) to generate initial indications 222 and subsequent indications 222 are compared against the initial indications and are included in the analysis 232.

In an example, the analysis 232 is generated using decision trees or decision rules describing inferences or conclusions to be drawn based on particular indications. For instance, a decision rule may specify that responsive to an indication 222 indicating that the recipient did not perceive a musical activity 10 having a vocalist of a particular vocal type, include in the analysis 232 that the recipient has difficulty perceiving musical activities 10 having a vocalist of the particular vocal type.

The analysis 232 can include metrics such as total number of engagements with musical activities 10, total number of missed engagements with musical activities 10, total number of engagements per day, rate of missed engagements, and an average grade of engagement. Additionally, trends in such metrics may be computed. The trends can reveal useful information in the auditory health of the recipient, such as determining improvement or decline in the recipient. Such trend information can be useful in the determining of treatment options for the recipient. Metrics may be segmented based on qualities of the musical signal, if it is detected or known, such as dominant frequencies, tempo, volume, genre, vocalist (e.g. male vocalist, female vocalist, age, languages spoken, accent, etc.). The segmentation can further enhance the analysis by allowing conclusions to be drawn on the basis of how the recipient is able to perceive specific musical features. For example, the analysis 232 can include metrics indicating that the recipient is better able to perceive music sung by vocalists having a baritone vocal range compared with a tenor vocal range.

Following operation 230, the flow of the process 200 can move to operation 240.

Operation 240 includes taking a treatment action 242 relating to the recipient based on the analysis 232. In an example, the treatment action 242 is an action relating to the treatment of a medical condition associated with the recipient's auditory system. Based on the analysis 232, various treatment actions 242 can be determined or recommended. In an example, the treatment action 242 includes reporting a performance quality of the auditory prosthesis 110 with respect to music, such as to a clinician (e.g., to help guide treatment) or caregiver (e.g., to help assure the caregiver that the auditory prosthesis 110 is functioning as intended). In an example, the treatment action 242 includes providing a metric estimating the recipient's ability to perceive music. In an example, the treatment action 242 includes recommending corrective actions.

In an example, the treatment action 242 includes recommending one or more pieces of music relative to recipient's ability to engage with music and a musical preference of the recipient. In an example, the treatment action 242 recommending corrective actions (e.g., reconfiguration, reprogramming, or revising the therapy, such as by advancing to bilateral prostheses from a unilateral prosthesis).

The treatment action 242 can also include using the analysis 232 (e.g., metrics thereof) as input to a music rehabilitation training program. The music rehabilitation program can take any of a variety of forms. In an example, the rehab game is the BRING BACK THE BEAT smartphone application by COCHLEAR LTD. The rehabilitation program can provide incrementally more challenging music (e.g., by proceeding from low beats-per-minute music to higher beats-per-minute music). The analysis 232 can be used to set a relative difficulty level of the music provided to the recipient. Further, the recipient's use of the rehabilitation program can be used as input data used to perform the processes described herein.

In an example rehabilitation program, a rehabilitator (e.g., a person or software performing a rehabilitation task) provides or recommends music to the recipient. Then the transducer signals 160 can be used to determine the recipient's music perception level and areas of weakness with respect to the music provided or recommended by the rehabilitator. Then the delivery of music content is modified based on the recipient's music perception level to train the recipient. For instance, the modifications can be focused on particular areas of weakness of the recipient's musical perception (e.g., as determined based on the analysis 232). The modifications can include increasing complexity of music provide or recommended by the rehabilitator (e.g., by adding or subtracting vocals or instruments from the music) or altering the quality of the audio signal of the music (e.g., by introducing breaks in the music or adding noise or distortion). The analysis 232 can include an estimate of the recipient's musical perception (e.g., the recipient's ability to perceive and engage with music), and recommend new pieces of music based thereon. For example, the new pieces of music can be based on an estimated difficulty of the musical signal relative to the individual's ability (e.g. slightly harder, but not dauntingly hard) and the recipient's musical preferences (e.g. genre). The relative difficulty of the new pieces of music can be increased.

In another example rehabilitation program, the rehabilitator prompts the recipient to sing or hum music content, and the performance is compared against an objective reference. In another example, the recipient can be instructed by the rehabilitator to identify a music content item. In yet another example, the rehabilitator can attempt to identify music content based on the recipient singing or humming the tune of the music content.

In another example, a gamification of the rehabilitation process is used by offering rewards to the recipient based on participation in the rehabilitation to increase engagement. In further examples, a recipient's musical preference is used to modify the rehabilitation program such that the recipient is more likely to enjoy and continue to participate in the rehabilitation.

In another treatment action, a fidelity for the individual's reproduction of a test musical piece by singing or humming based on the musical piece. While the rehabilitation program can be configured to improve the recipient's music perception directly, indirect approaches can be used as well, such as by measuring and training the recipient's singing or pitch-articulation ability.

In some examples, operation 240 includes operation 244.

Operation 244 includes modifying a treatment operation of the auditory prosthesis 110 by changing one or more settings of the auditory prosthesis 110. For example, based on the analysis 232, it can be ascertained that the auditory prosthesis settings 114 are sub-optimally causing hearing percepts in the recipient with respect to music and that one or more changes to the auditory prosthesis settings 114 can improve the performance of the auditory prosthesis with respect to music. Based on the determination, the one or more changes can be provided to the recipient or a clinician (e.g., by way of a report) or to the auditory prosthesis 110 itself (e.g., via the auditory prosthesis application). The auditory prosthesis settings 114 are then changed, which modifies the ongoing operation of the auditory prosthesis 110. In some examples, scene-specific auditory prosthesis settings 114 are changed. For instance, the auditory prosthesis settings 114 associated with a music mode (e.g., as determined by a scene classifier of the auditory prosthesis) are changed but not in other modes. This scene-specific approach can be advantageous because changes that improve the capability of the auditory prostheses 110 to produce music-based hearing percepts understandable by a recipient can have a concomitant detrimental effect on the capability of the auditory prostheses 110 to produce speech-based hearing percepts understandable by the recipient.

Example Processes—Second Example Process

FIG. 3 illustrates a second example process 300 for taking a treatment action with respect to the musical perception of a recipient of an auditory prosthesis. In examples, the process 300 begins with operation 310.

Operation 310 includes maintaining, at the server 170, one or more templates 180 defining an association between transducer signals 160 and musical perception. Maintaining the templates 180 can include storing the templates 180 in a usable form in memory accessible to the server 170 (e.g., memory 804). In examples, operation 310 includes operation 312.

Operation 312 includes generating or updating the one or more templates 180. In an example, the operation 312 includes receiving one or more templates 180 from a user (e.g., a clinician). The operation 312 can include using transducer signals 160 relating to a plurality of individuals to generate or update the one or more templates 180. For example, the operation 312 can include aggregating transducer signals 160 relating to a plurality of individuals and manually or automatically generating templates 180 thereon. For instance, using the aggregated transducer signals 160, it can be determined that movement data having particular characteristics is indicative of responding to a musical activity 10. So a template 180 can be generated specifying that if movement data having those particular characteristics are is received in the future a determination should be made of an indication 222 that the recipient is able to perceive a musical activity. The one or more templates 180 can be generated using a statistical analysis of the received transducer signals 160.

In examples, operation 312 includes training one or more machine-learning frameworks 184 of the template 180. Training the machine-learning framework 184 can occur in any of a variety of different ways depending on the machine-learning model type used. Generally the training can occur in the following manner. First, training data is obtained for use in training the machine-learning model. The training data is typically a set of human- or machine-curated data having known training input and desired training output usable to train the machine-learning framework. In the case of operation 312, the training data can include curated transducer signals 160 from many different individuals and actual or expected output. In general, the training includes providing a training input as input into the machine-learning learning framework 184 using the interface of the machine-learning framework 184. The machine-learning framework 184 processes the input using the machine-learning model and produces an output. A loss function is then used to calculate a loss value based on a comparison between the actual output of the machine-learning model and the expected output (e.g., the training output that corresponds to the training input provided). Attributes of the machine-learning model (e.g., weights of connections in the machine-learning model) are modified based on a loss value, thereby training the model. This training process continues for an amount of training data until the loss value is sufficiently small. In examples, the trained machine-learning framework 184 is validated using validation input-output data (e.g., data having desired outputs corresponding to particular inputs that are different from the training data), and after successful validation, the machine-learning framework 184 is used in production. A similar process can be used to train one or more machine-learning frameworks 184 to produce output relating to the analysis 232 or the treatment action 242.

Following operation 310, the process 300 can move to operation 320.

Operation 320 includes receiving, at the server 170, recipient transducer signals 160. For example, the transducer signals 160 can be received from the computing device 120 or directly from the transducers 150 themselves. The recipient transducer signals 160 are associated with a recipient of an auditory prosthesis 110. The transducer signals 160 can be received from one or more transducers 150 of one or more devices.

In some examples, the transducer signals 160 are pushed to the server 170 from the transducers 150 or a device associated therewith. In other examples, the server 170 sends a request to the transducers 150 or a device associated therewith to obtain the transducer signals 160.

In some examples, the computing device 120 collects the transducer signals 160 prior to being sent to the server 170. In some examples, the computing device 120 periodically obtains readings from the computing device transducer set 122 and other transducers 150 or devices associated therewith. In some examples, the computing device 120 obtains the readings responsive to a request (e.g., a request received from the auditory prosthesis application 124). The computing device 120 can collect the transducer signals 160 at a variety of frequencies and the amount of transducer signals 160 can likewise vary. For instance, in some examples, the obtaining and transmitting of the transducer signals 160 occurs without substantial delay. In other examples, the devices that include transducers 150 (e.g., the auditory prosthesis 110) can obtain and store the transducer signals 160 in batches and transmits the transducer signals 160 less frequently to the computing device 120 or the server 170.

Following operation 320, the flow of the process 300 can move to operation 330.

Operation 330 includes using the template 180 and the recipient transducer signals 160 to generate an analysis 232 of the recipient's musical perception, such as is described in relation to operation 220 and operation 230 with regard to FIG. 2. In some examples, operation 330 includes operation 332 and operation 334. In some examples, operation 330 includes operation 336 and operation 338.

Operation 332 providing the recipient transducer signals 160 to a trained machine-learning framework 184 as input. The operation 332 can include, for example, selecting a machine-learning framework 184 from one or more machine-learning frameworks 184. The selecting can be based on, for example, types of transducer signals 160. In some examples, more than one machine-learning framework 184 is selected. In some examples, transducer signals 160 from multiple different transducers 150 can be combined together (e.g., concatenated) to form the input data into the machine-learning framework. The operation 332 can further include pre-processing the transducer signals 160 for use with the machine-learning framework 184. For instance, the transducer signals 160 can be placed into a particular format for the machine-learning framework 184. For instance the machine-learning framework 184 can be configured to receive input data in a vector format and the transducer signals 160 can be converted into such a format in preparation for providing the transducer signals 160 as input. In examples, the conversion and the providing can be performed using or in cooperation with an interface of the machine-learning framework 184. In an example, the interface provides functions that convert the transducer signals 160 into a useful format and then provide the converted signals as input into a machine-learning model of the machine-learning framework 184. Following operation 332, the flow of the process 300 can move to operation 334.

Operation 334 includes receiving 334 an indication 222 of the recipient's ability to receive music as output from the trained machine-learning framework 184. For example, the interface of the machine-learning framework 184 can receive the output from the model, convert the output into the indication 222 and then provide the indication 222 as output. The indication 222 can then be used to generate the analysis 232, such as using one or more of the techniques described in conjunction with operation 230.

Operation 336 includes comparing the recipient transducer signals 160 to the threshold 182. Following operation 336, the flow of the process can move to operation 338. Operation 338 includes: responsive 338 to the recipient transducer signals 160 satisfying the threshold 182, determining that the recipient is able to perceive music.

Following operation 330, the flow of the process 300 can move to operation 240.

Operation 240 includes taking a treatment action 242 relating to the auditory prosthesis 110 based on the analysis 232. Operation 240 can have the properties of operation 240 as described above in relation to process 200.

Example Processes—Third Example Process

FIG. 4 illustrates a third example process 400 for taking a treatment action with respect to the musical perception of a recipient of an auditory prosthesis. In the illustrated example, the process 400 begins with operation 410.

Operation 410 includes collecting transducer signals 160 from one or more transducers 150 associated with a recipient of an auditory prosthesis 110. The operation 410 can include one or more techniques similar to those described in operation 320 herein. The transducer signals 160 can include signals from a variety of different kinds of transducers. In an example, the operation 410 includes receiving movement sensor signals from one or more movement sensors. In an example, receiving movement sensor signals can include receiving accelerometer signals from an accelerometer of the auditory prosthesis, receiving gyroscope signals from a gyroscope of the auditory prosthesis, receiving accelerometer signals from an accelerometer of a mobile device of the recipient, or receiving gyroscope signals from a gyroscope of a mobile device of the recipient. In an example, the operation 410 includes receiving body noise sensor signals from an implanted microphone. In an example, the operation 410 includes receiving implanted electrode sensor signals from an implanted electrode. In an example, the operation 410 includes receiving external microphone signals from an external microphone. Following operation 410, the flow of the process 400 moves to operation 420.

Operation 420 includes generating indications 222 of the recipient's musical perception using the transducer signals 160. The operation 420 can include one or more techniques similar to those described in operation 330 herein. In an example, the movement sensor signals are used to generate an indication of hand motion. In an examples, the body noise sensor signals are used to generate an indication of blood flow activity of the recipient. In addition or instead, the body noise sensor signals can be used to generate an indication 222 of respiratory activity of the recipient. In still further examples, the body noise sensor signals can be used to generate an indication 222 of recipient voice activity. In some examples, the implanted electrode sensor signals are used to generating an indication of brainstem activation. In other examples, the implanted electrode signals are used to generate an indication 222 of midbrain or cortical activation. In examples, the external microphone signals are used to generate an indication 222 of the recipient's voice activity. Following operation 420, the flow of the process 400 moves to operation 430.

Operation 430 includes generating an analysis 232 of the recipient's musical perception using the indications 222. Operation 430 can include one or more techniques similar to those described in operation 340 herein. In an example, generating the analysis 232 includes comparing the indications 222 to one or more templates. In an example, generating the analysis 232 includes comparing the indications 222 to features of a piece of music (e.g., a piece of music associated with the musical activity 10). In an example, generating the analysis 232 includes comparing the indications 222 to other indications taken from other individuals. In an example, the analysis 232 includes a metric. The metric can include, for example, a metric describing a number engagements with music, a metric describing a rate of missed engagements; and a metric describing an average grade of engagement. In an example, the metric is classified according to musical qualities, such as dominant musical frequencies, a musical tempo, a music volume, a music genre, and a musical vocalist type. Following operation 430, the flow of the process can move to operation 240.

Operation 240 includes taking a treatment action 242 relating to the auditory prosthesis based on the analysis 232. Operation 240 can have the properties of operation 240 as described above in relation to process 200.

Example Auditory Prostheses

As previously described, the auditory prosthesis 110 can take any of a variety of forms. Examples of these forms are described in more detail in FIGS. 5-7, below. For instance, the auditory prosthesis 110 may be the cochlear implant system 510 of FIG. 5, the percutaneous bone conduction device 600 of FIG. 6, or the transcutaneous bone conduction device 700 of FIG. 7. These different auditory prostheses 110 can benefit from use with the systems and processes described above. For instance, the process 200 can be used to customize the auditory prosthesis 110 to function an in improved manner at least with respect to causing hearing percepts based on musical input.

Example Auditory Prostheses—Cochlear Implant System

Figure 5:
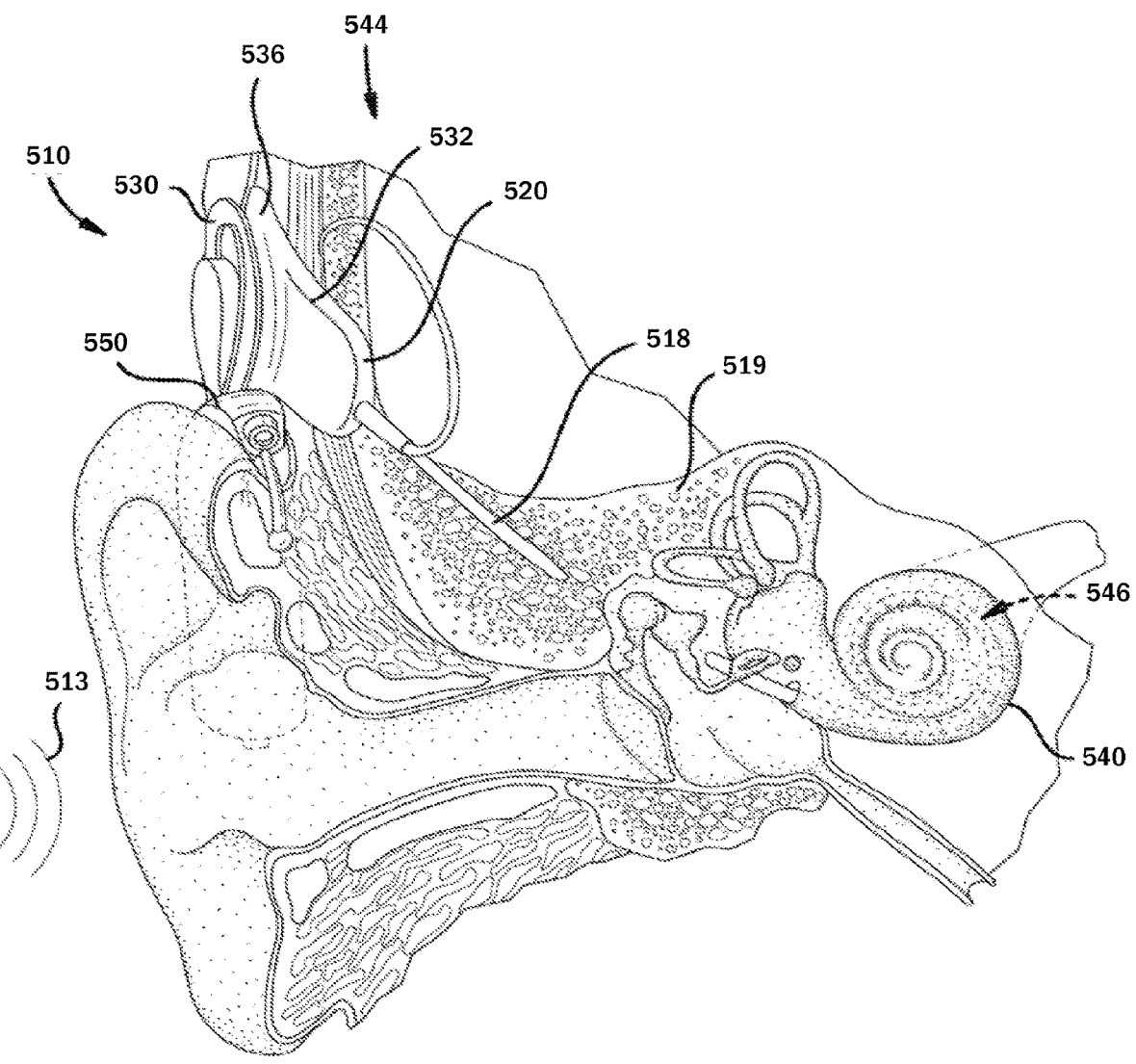
FIG. 5 illustrates an example cochlear implant system that can benefit from the use of technologies described herein.

FIG. 5 illustrates an example cochlear implant system 510 that can benefit from use of the technologies disclosed herein. The cochlear implant system 510 includes an implantable component 544 typically having an internal receiver/transceiver unit 532, a stimulator unit 520, and an elongate lead 518. The internal receiver/transceiver unit 532 permits the cochlear implant system 510 to receive signals from and/or transmit signals to an external device 550. The external device 550 can be a button sound processor worn on the head that includes a receiver/transceiver coil 530 and sound processing components. Alternatively, the external device 550 can be just a transmitter/transceiver coil in communication with a behind-the-ear device that includes the sound processing components and microphone.

The implantable component 544 includes an internal coil 536, and preferably, a magnet (not shown) fixed relative to the internal coil 536. The magnet can be embedded in a pliable silicone or other biocompatible encapsulant, along with the internal coil 536. Signals sent generally correspond to external sound 513. The internal receiver/transceiver unit 532 and the stimulator unit 520 are hermetically sealed within a biocompatible housing, sometimes collectively referred to as a stimulator/receiver unit. Included magnets (not shown) can facilitate the operational alignment of an external coil 530 and the internal coil 536, enabling the internal coil 536 to receive power and stimulation data from the external coil 530. The external coil 530 is contained within an external portion. The elongate lead 518 has a proximal end connected to the stimulator unit 520, and a distal end 546 implanted in a cochlea 540 of the recipient. The elongate lead 518 extends from stimulator unit 520 to the cochlea 540 through a mastoid bone 519 of the recipient. The elongate lead 518 is used to provide electrical stimulation to the cochlea 540 based on the stimulation data. The stimulation data can be created based on the external sound 513 using the sound processing components and based on the auditory prosthesis settings 114.

In certain examples, the external coil 530 transmits electrical signals (e.g., power and stimulation data) to the internal coil 536 via a radio frequency (RF) link. The internal coil 536 is typically a wire antenna coil having multiple turns of electrically insulated single-strand or multi-strand platinum or gold wire. The electrical insulation of the internal coil 536 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Example Auditory Prostheses—Percutaneous Bone Conduction Device

Figure 6:
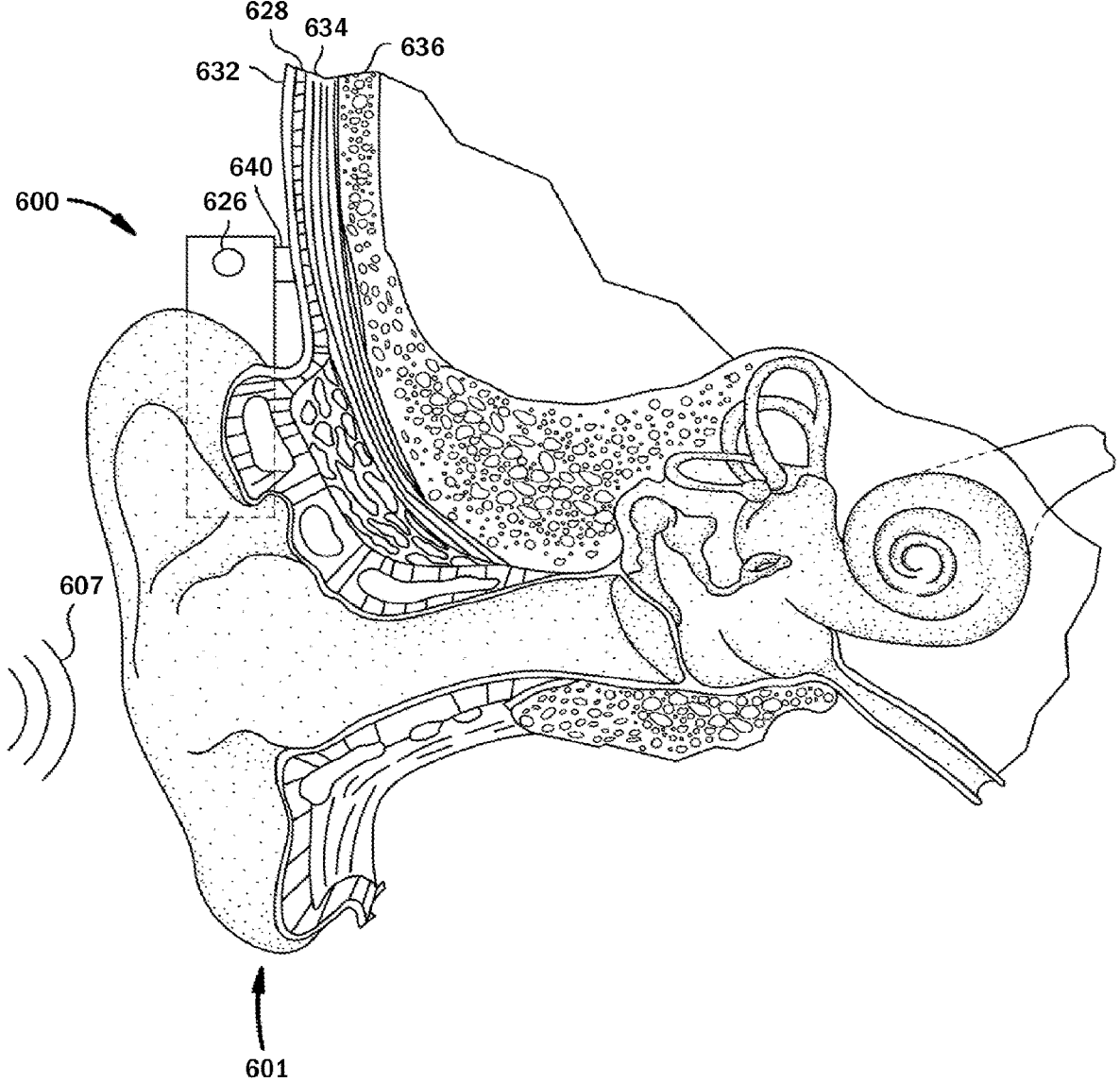
FIG. 6 is a view of an example percutaneous bone conduction device that can benefit from use of the technologies disclosed herein.

FIG. 6 is a view of an example of a percutaneous bone conduction device 600 that can benefit from use of the technologies disclosed herein. For example, the auditory prosthesis settings 114 of the device 600 can be customized using one or more aspects of disclosed technology. The bone conduction device 600 is positioned behind an outer ear 601 of a recipient of the device. The bone conduction device 600 includes a sound input element 626 to receive sound signals 607. The sound input element 626 can be a microphone, telecoil or similar. In the present example, the sound input element 626 may be located, for example, on or in the bone conduction device 600, or on a cable extending from the bone conduction device 600. Also, the bone conduction device 600 comprises a sound processor (not shown), a vibrating electromagnetic actuator and/or various other operational components.

More particularly, the sound input element 626 converts received sound signals into electrical signals. These electrical signals are processed by the sound processor. The sound processor generates control signals that cause the actuator to vibrate. In other words, the actuator converts the electrical signals into mechanical force to impart vibrations to a skull bone 636 of the recipient. The conversion of the electrical signals into mechanical force can be based on the auditory prosthesis settings 114, such that different auditory prosthesis settings 114 may result in different mechanical force being generated from a same sound signal 607.

The bone conduction device 600 further includes a coupling apparatus 640 to attach the bone conduction device 600 to the recipient. In the illustrated example, the coupling apparatus 640 is attached to an anchor system (not shown) implanted in the recipient. An exemplary anchor system (also referred to as a fixation system) may include a percutaneous abutment fixed to the skull bone 636. The abutment extends from the skull bone 636 through muscle 634, fat 628 and skin 632 so that the coupling apparatus 640 may be attached thereto. Such a percutaneous abutment provides an attachment location for the coupling apparatus 640 that facilitates efficient transmission of mechanical force.

Example Auditory Prostheses—Transcutaneous Bone Conduction Device

Figure 7:
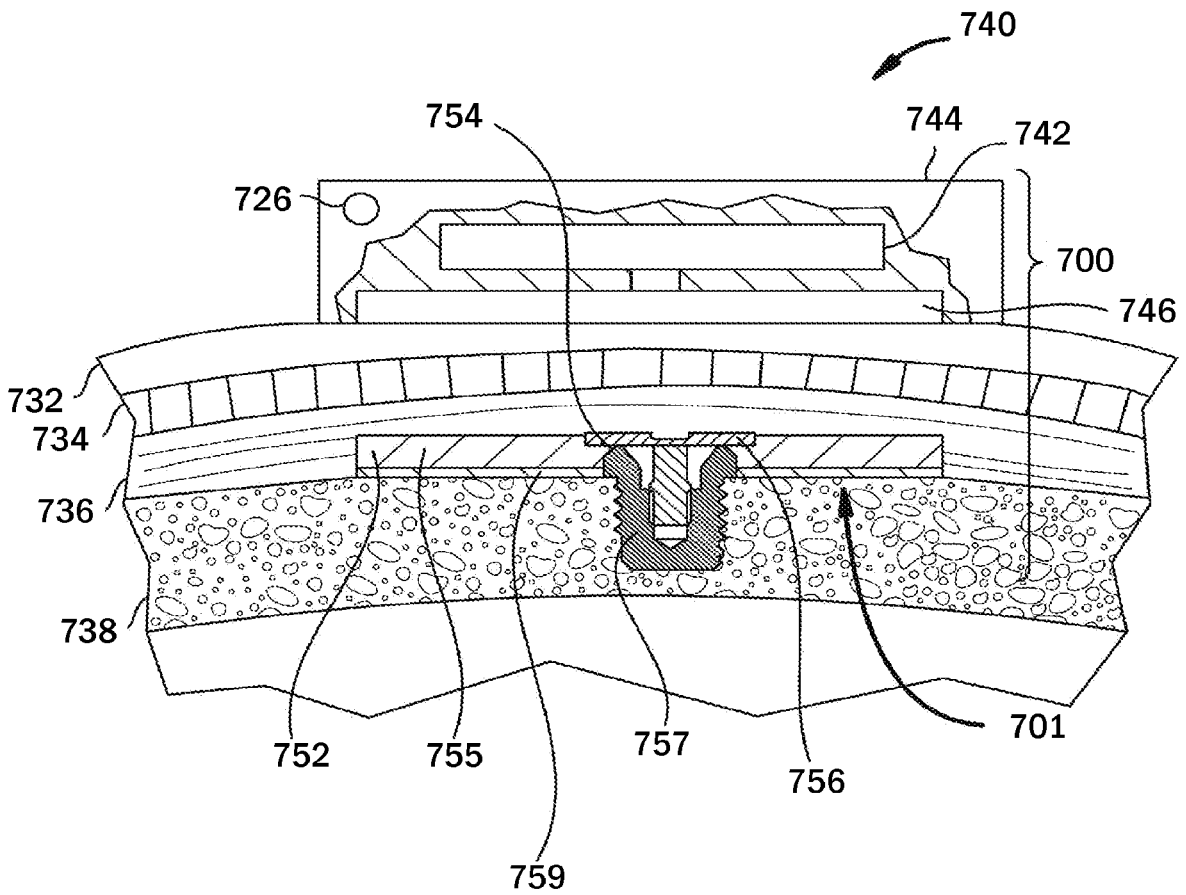
FIG. 7 illustrates an example transcutaneous bone conduction device having a passive implantable component that can benefit from use of the technologies disclosed herein.

FIG. 7 illustrates an example of a transcutaneous bone conduction device 700 having a passive implantable component 701 that can benefit from use of the technologies disclosed herein. The transcutaneous bone conduction device includes an external device 740 and an implantable component 701. The implantable component 701 includes a passive plate 755 mounted on the bone 738 and is transcutaneously coupled with a vibrating actuator 742 located in a housing 744 of the external device 740. The plate 755 may be in the form of a permanent magnet or in another form that generates or is reactive to a magnetic field, or otherwise permits the establishment of magnetic attraction between the external device 740 and the implantable component 750 sufficient to hold the external device 740 against the skin 732 of the recipient.

In an example, the vibrating actuator 742 is a component that converts electrical signals into vibration. In operation, sound input element 726 converts sound into electrical signals. Specifically, the transcutaneous bone conduction device 700 provides these electrical signals to a vibrating actuator 742, or to a sound processor (not shown) that processes the electrical signals, and then provides those processed signals to a vibrating actuator 742. The manner in which the sound processor processes the electrical signals can be modified based on the auditory prosthesis settings 114. The vibrating actuator 742 converts the electrical signals (processed or unprocessed) into vibrations. Because the vibrating actuator 742 is mechanically coupled to a plate 746, the vibrations are transferred from the vibrating actuator 742 to the plate 746. An implanted plate assembly 752 is part of the implantable component 750, and is made of a ferromagnetic material that may be in the form of a permanent magnet, that generates and/or is reactive to a magnetic field, or otherwise permits the establishment of a magnetic attraction between the external device 740 and the implantable component 750 sufficient to hold the external device 740 against the skin 732 of the recipient. Accordingly, vibrations produced by the vibrating actuator 742 of the external device 740 are transferred from plate 746 across the skin 732, fat 734, and muscle 736 to the plate 755 of the plate assembly 752. This may be accomplished as a result of mechanical conduction of the vibrations through the tissue, resulting from the external device 740 being in direct contact with the skin 732 and/or from the magnetic field between the two plates 746, 755. These vibrations are transferred without penetrating the skin 732 with a solid object such as an abutment.

As may be seen, the implanted plate assembly 752 is substantially rigidly attached to a bone fixture 757 in this example. But other bone fixtures may be used instead in this and other examples. In this regard, the implantable plate assembly 752 includes a through hole 754 that is contoured to the outer contours of the bone fixture 757. The through hole 754 thus forms a bone fixture interface section that is contoured to the exposed section of the bone fixture 757. In an example, the sections are sized and dimensioned such that at least a slip fit or an interference fit exists with respect to the sections. A plate screw 756 is used to secure plate assembly 752 to the bone fixture 757. The head of the plate screw 756 can be larger than the hole through the implantable plate assembly 752, and thus the plate screw 756 positively retains the implantable plate assembly 752 to the bone fixture 757. The portions of plate screw 756 that interface with the bone fixture 757 substantially correspond to an abutment screw detailed in greater detail below, thus permitting the plate screw 756 to readily fit into an existing bone fixture used in a percutaneous bone conduction device. In an example, the plate screw 756 is configured so that the same tools and procedures that are used to install and/or remove an abutment screw from the bone fixture 757 can be used to install and/or remove the plate screw 756 from the bone fixture 757. In some examples, there may be a silicone layer 759 disposed between the plate 755 and bone 738.

Example Computing System

Figure 8:
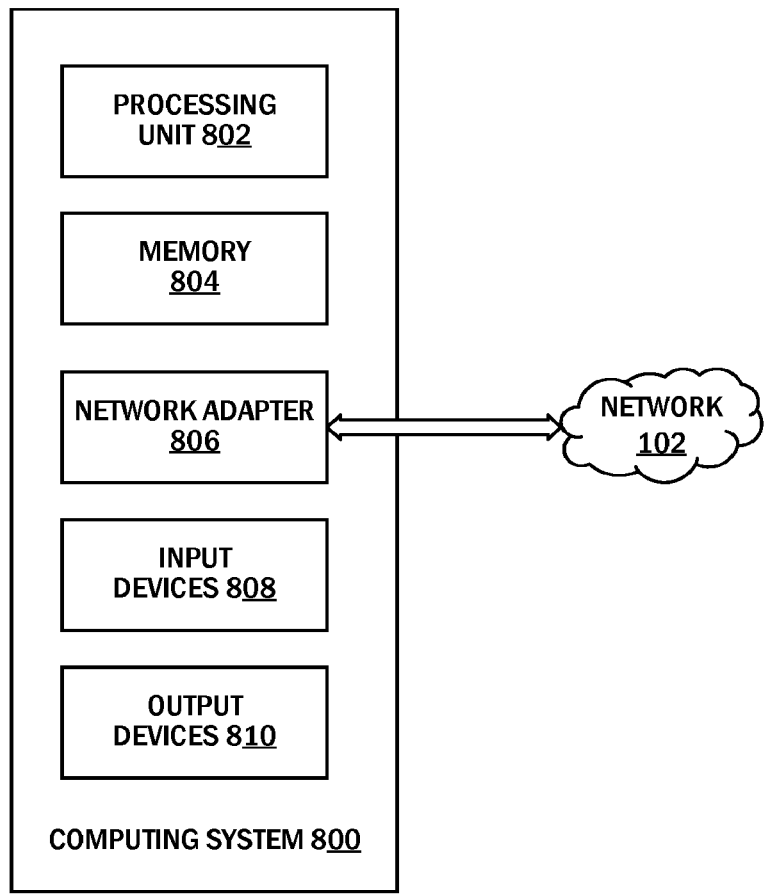
FIG. 8 illustrates an example computing system with which one or more of the disclosed examples can be implemented.

FIG. 8 illustrates an example of a suitable computing system 800 with which one or more of the disclosed examples can be implemented. Computing systems, environments, or configurations that can be suitable for use with examples described herein include, but are not limited to, personal computers, server computers, hand-held devices, laptop devices, multiprocessor systems, microprocessor-based systems, programmable consumer electronics (e.g., smart phones), network PCs, minicomputers, mainframe computers, tablets, distributed computing environments that include any of the above systems or devices, and the like. The computing system 800 can be a single virtual or physical device operating in a networked environment over communication links to one or more remote devices. The remote device can be an auditory prosthesis (e.g., the auditory prosthesis 110), a personal computer, a server, a router, a network personal computer, a peer device or other common network node. In examples, the computing device 120 and the server 170 includes one or more components or variations of components of the computing system 800. Further, in some examples, the auditory prosthesis 110 includes one or more components of the computing system 800.

In its most basic configuration, computing system 800 includes at least one processing unit 802 and memory 804.

The processing unit 802 includes one or more hardware or software processors (e.g., Central Processing Units) that can obtain and execute instructions. The processing unit 802 can communicate with and control the performance of other components of the computing system 800.

The memory 804 is one or more software- or hardware-based computer-readable storage media operable to store information accessible by the processing unit 802. The memory 804 can store, among other things, instructions executable by the processing unit 802 to implement applications or cause performance of operations described herein, as well as other data. The memory 804 can be volatile memory (e.g., RAM), non-volatile memory (e.g., ROM), or combinations thereof. The memory 804 can include transitory memory or non-transitory memory. The memory 804 can also include one or more removable or non-removable storage devices. In examples, the memory 804 can include RAM, ROM, EEPROM (Electronically-Erasable Programmable Read-Only Memory), flash memory, optical disc storage, magnetic storage, solid state storage, or any other memory media usable to store information for later access. In examples, the memory 804 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 804 can include wired media such as a wired network or direct-wired connection, and wireless media such as acoustic, RF, infrared and other wireless media or combinations thereof.

In the illustrated example, the system 800 further includes a network adapter 806, one or more input devices 808, and one or more output devices 810. The system 800 can include other components, such as a system bus, component interfaces, a graphics system, a power source (e.g., a battery), among other components.

The network adapter 806 is a component of the computing system 800 that provides network access. The network adapter 806 can provide wired or wireless network access and can support one or more of a variety of communication technologies and protocols, such as ETHERNET, cellular, BLUETOOTH, near-field communication, and RF (Radiofrequency), among others. The network adapter 806 can include one or more antennas and associated components configured for wireless communication according to one or more wireless communication technologies and protocols.

The one or more input devices 808 are devices over which the computing system 800 receives input from a user. The one or more input devices 808 can include physically-actuatable user-interface elements (e.g., buttons, switches, or dials), touch screens, keyboards, mice, pens, and voice input devices, among others input devices.

The one or more output devices 810 are devices by which the computing system 800 is able to provide output to a user. The output devices 810 can include, displays, speakers, and printers, among other output devices.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. For examples, while certain technologies described herein were primarily described in the context of auditory prostheses (e.g., cochlear implants), technologies disclosed herein are applicable to medical devices generally (e.g., medical devices providing pain management functionality or therapeutic electrical stimulation, such as deep brain stimulation). In general, additional configurations can be used to practice the processes and systems herein and/or some aspects described can be excluded without departing from the processes and systems disclosed herein. Further, the techniques described herein can be applicable to determining a recipient's response to other stimuli, such as visual stimuli, tactile stimuli, olfactory stimuli, taste stimuli, or another stimuli.

Likewise, the devices used herein need not be limited to auditory prostheses and can be other medical devices configured to support a human sense, such as bionic eyes.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a process are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

The invention claimed is:

1. A method comprising:
   determining an occurrence of an audible activity proximate a recipient of an auditory device using first transducer signals from one or more first transducers;
   determining an indication of an ability of the recipient to perceive the audible activity using second transducer signals from one or more second transducers; and
   generating, via the auditory device, an output reflecting the ability of the recipient to perceive the audible activity.

2. The method of claim 1, further comprising determining an overall quality of life of the recipient based on a determined reduced ability of the recipient to perceive the audible activity.

3. The method of claim 2, wherein determining the overall quality of life of the recipient comprises determining a plurality of performance metrics related to the recipient.

4. The method of claim 3, wherein at least one of the plurality of performance metrics is unrelated to music.

5. The method of claim 1, wherein the output changes one or more settings of the auditory device.

6. The method of claim 1, further comprising:
   determining the occurrence of the audible activity proximate the recipient has ceased; and
   suspending determination of the indication of the ability of the recipient to perceive the audible activity in response to determining the occurrence of the audible activity has ceased.

7. The method of claim 6, further comprising:
   identifying a visual cue; and
   determining the indication of the ability of the recipient to perceive the audible activity based on the visual cue.

8. The method of claim 7, further comprising:
   determining a response of the recipient is caused by the visual cue rather than by the audible activity, wherein determining the indication of the ability of the recipient to perceive the audible activity based on the visual cue comprises determining a reduced ability of the recipient to perceive the audible activity in response to determining the response of the recipient is caused by the visual cue rather than by the audible activity.

9. A method comprising:
   determining an occurrence of a sensory input to a recipient of a sensory device using first transducer signals from one or more first transducers;
   determining an indication of an ability of the recipient to perceive the sensory input using second transducer signals from one or more second transducers; and
   generating, with the sensory device, an output reflecting the ability of the recipient to perceive the sensory input.

10. The method of claim 9, wherein the output comprises recommendations of one or more pieces of music relative to the ability of the recipient to perceive the sensory input.

11. The method of claim 9, wherein determining the indication of the ability of the recipient to perceive the sensory input comprises comparing a repetitive behavior of the recipient to a threshold range.

12. A wearable device comprising:
   one or more first transducers configured to detect an input signal indicative of music; and
   one or more second transducers configured to determine movement of a recipient of the wearable device in presence of music indicated by the input signal.

13. The wearable device of claim 12, wherein the input signal comprises a stream of musical data.

14. The wearable device of claim 12, wherein the input signal comprises an audio transducer signal of a sonic environment proximate the recipient.

15. The wearable device of claim 14, further comprising a computing device configured to compare a property of the audio transducer signal to a threshold to determine the presence of music proximate the recipient.

16. The wearable device of claim 15, wherein the property comprises a frequency, an amplitude modulation, a spectral spread, or any combination thereof.

17. The wearable device of claim 12, wherein operation of the one or more second transducers is suspended based on an absence of the input signal indicative of music detected by the one or more first transducers.

18. The wearable device of claim 12, wherein the movement of the recipient determined by the one or more second transducers comprises a respiratory or blood related biometric activity of the recipient.

19. The wearable device of claim 12, wherein the movement of the recipient determined by the one or more second transducers comprises a neural activation of the recipient.

20. A non-transitory, computer-readable medium comprising instructions that, when executed by one or more processors, are configured to cause the one or more processors to perform operations comprising:
   collecting transducer signals from one or more transducers associated with a recipient of an auditory device;
   generating an indication of a musical perception of the recipient using the transducer signals;
   generating an analysis of the musical perception of the recipient using the indication; and recommending one or more pieces of music to the recipient based on the musical perception of the recipient using the analysis.

21. The non-transitory, computer-readable medium of claim 20, wherein the indication of the musical perception of the recipient comprises a voice activity, and the analysis of the musical perception of the recipient comprises comparing the voice activity to musical activity proximate the recipient.

22. The non-transitory, computer-readable medium of claim 20, wherein the indication of the musical perception of the recipient comprises a repetitive behavior of the recipient, and the analysis of the musical perception of the recipient comprises comparing a frequency of the repetitive behavior to a threshold.

23. The non-transitory, computer-readable medium of claim 22, wherein the repetitive behavior of the recipient comprises head movement of the recipient.

24. The non-transitory, computer-readable medium of claim 20, wherein the analysis of the musical perception of the recipient comprises comparing the indication of the musical perception of the recipient to a genre of musical activity proximate the recipient.

\* \* \* \* \*